United States Patent
Bland

(10) Patent No.: US 6,638,613 B1
(45) Date of Patent: Oct. 28, 2003

(54) THERAPEUTICALLY ENHANCED SALIVA-ACTIVATABLE CELLULOSIC PRODUCT

(76) Inventor: Todd A. Bland, 13708 Frederick Ave., Omaha, NE (US) 68138

( * ) Notice: Subject to any disclaimer, the term of this patent is extended or adjusted under 35 U.S.C. 154(b) by 0 days.

(21) Appl. No.: 10/279,499

(22) Filed: Oct. 25, 2002

(51) Int. Cl.$^7$ ................................................ B32B 15/04
(52) U.S. Cl. ...................................... 428/350; 428/34.3
(58) Field of Search ........................ 428/350, 34.3; 424/484, 485, 486

(56) References Cited

U.S. PATENT DOCUMENTS 4,832,057 A * 5/1989 Bale et al. .................... 131/73
5,532,293 A * 7/1996 Landis ........................ 523/210

* cited by examiner

*Primary Examiner*—Harold Pyon
*Assistant Examiner*—Jane Rhee

(57) ABSTRACT

Therapeutically Enhanced Saliva-Activatable Cellulosic Product comprising a conventional flexible cellulosic paper item having parallel horizontal broad surfaces including an upper-surface and a lower-surface and which surfaces are intersected by an upright longitudinal-edge, said conventional cellulosic paper item being non-conventionally augmented at the upper-surface thereof and nearby along a longitudinal-edge with a saliva-activatable therapeutic-layer carrying at the topical-surface thereof a selectable therapeutic-agent. Among such generally available conventional cellulosic paper items, and thus available for saliva-activatable therapeutic enhance, are conventional rollably secureable cigarette papers, mailing envelopes, epidermally-adherent body bandages, etc.

10 Claims, 2 Drawing Sheets

THERAPEUTICALLY ENHANCED SALIVA-ACTIVATABLE CELLULOSIC PRODUCT

BACKGROUND OF THE INVENTION

Flexible cellulosic paper items (such as cigarette papers, mailing envelopes, and the like) are sometimes peripherally provided with moistable adhesive which is orally activatable through the user's tongue and/or lips. Although known through other and pharmaceutical art is that the human tongue and/or lips are employable for ingesting medicines, pharmaceuticals and other therapeutic agents. However, the prior art has not heretofore suggested that therapeutic agents might be ingestibly provided through the moistable adhesive localized coatings of flexible cellulosic paper items.

GENERAL OBJECTIVES OF THE INVENTION

It is the general objective of the present invention to augment cigarette papers and other orally sensitive utilitarian conventional cellulosic paper item of the prior art and at its moistable adhesive peripheral portion, with a therapeutic agent whereby whenever the user orally activates the paper item's adhesive area, therapeutic agent will be concurrently ingested into efficaceously into the user.

GENERAL STATEMENT OF THE INVENTION

With the above mentioned general objective in view, and together with other ancillary and related objectives which will become more apparent as this description proceeds, the Therapeutically Enhanced Saliva-Activatable Cellulosic Products of the present invention, and especially for cigarette papers of the prior art, generally retains en toto conventional cigarette papers (e.g. 10, 10A, of FIGS. 1 and 2) that are conventionally longitudinally edgewise provided with a saliva;moistable stripwise adhesive-layer (20), but which prior art papers (10, 10A) alongside a first-strip (20) being adherently augmented with a second-strip (35, 45) topically carrying therat a saliva ingestable therapeutic agent.

BRIEF DESCRIPTION OF THE DRAWING

In the drawing, wherein like characters refer to like parts in the several views, and in which.

As a representative example-for the prior art environment of the Therapeutically Enhanced Saliva-Activatable Cellulosic Product of the present invention.

Figure 5:
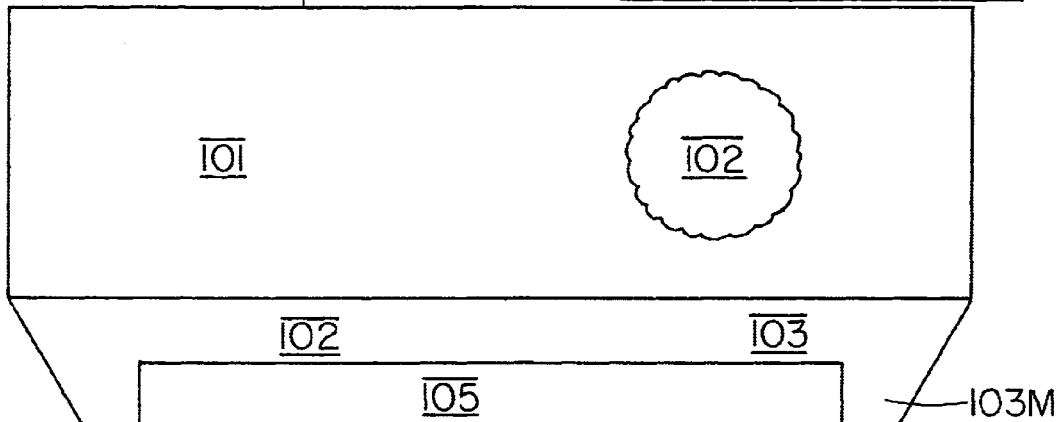
Figure 6:
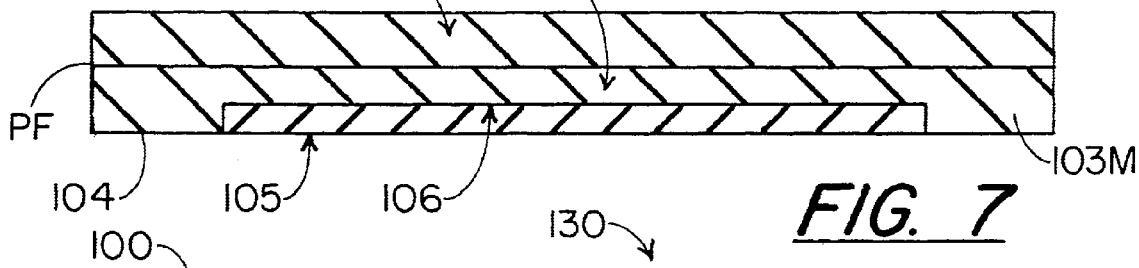
Figure 7:
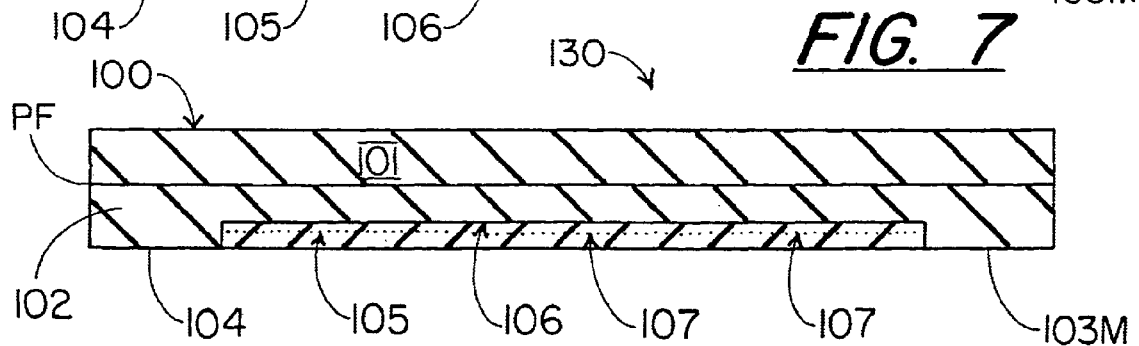

As another representative prior art environment is the FIG. 5 top plan view of a conventional mailing envelope (100) ;

FIG. 6 is a sectional elevational view taken along line 6—6 of the FIG. 5 environmental prior art situation (100); and FIG. 7 is a sectional elevational view, akin to FIG. 6, but embellished at 107 to indicate another mode (130) of the "therapeutically enhanced saliva-activatable cellulosic product" of the present invention.

DETAILED DESCRIPTION OF THE DRAWING

Figure 1:
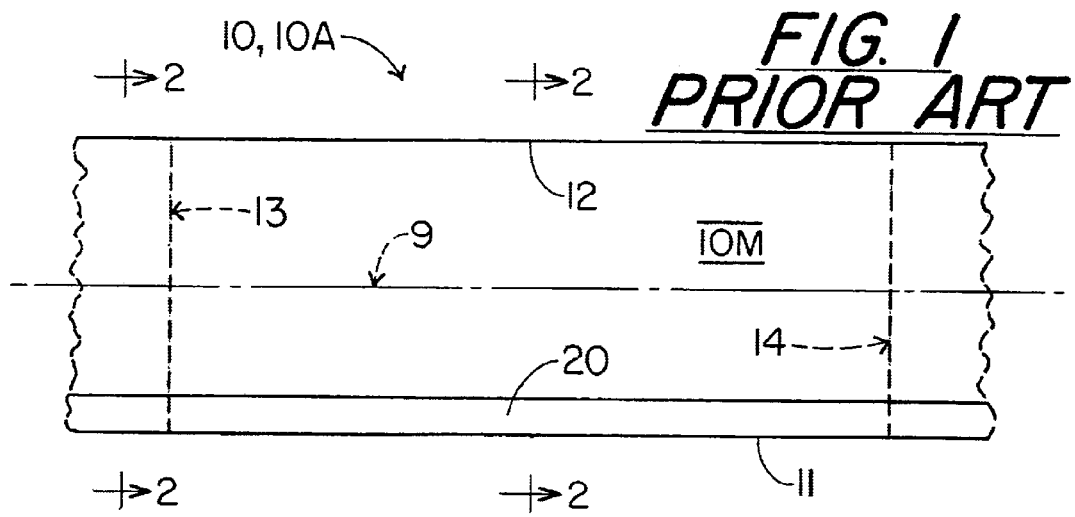
FIG. 1 is a top plan view of a conventional cellulosic cigarette paper (10, 10A) of the prior art.
Figure 2:
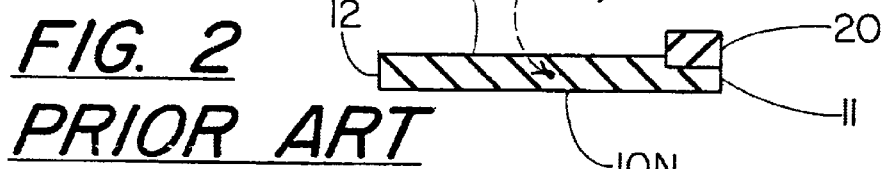
FIG. 2 is a sectional elevational view taken along lines 2—2 of FIG. 1.

Drawing FIGS. 1 and 2 refer to a prior art orally utilitarian cellulosic item provided peripherally with moistable adhesive and in a cigarette paper selectable classification (10, 10A) that extends directionally longitudinally along a central-axis 9, has parallel broad surfaces including an upper-surface 10M and a lower-surface 10N, and having longitudinally extending upright longitudinal—edges 11 and 12 flanking central-axis 9. Extending along one such longitudinal—edge (e.g. 11) and atop upper-surface (10M) is a saliva moistable first-strip adhesive-layer (20), whereby the cigarette paper might be longitudinally rolled about tobacco placed upon upper-surface 10M and thence adhesively rollably secured (20) to provide mass-productionally and/or singly adhesively secured smokable cigarettes. Dotted lines 13 and 14 indicate the selectable situation of a single sheet (10A) of lengthwise cigarette paper.

Figure 3:
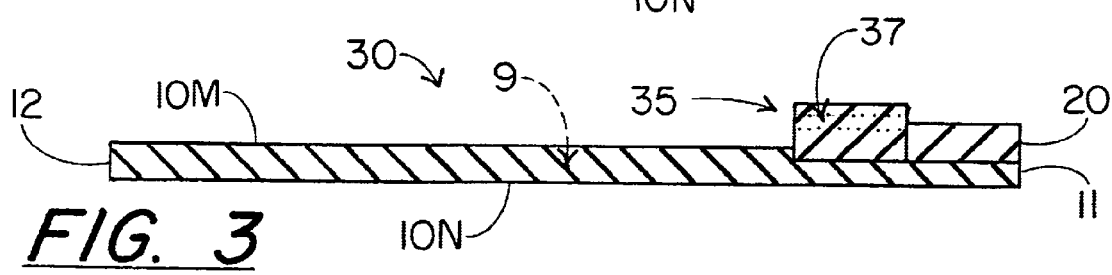
FIG. 3 is a sectional elevational view, similar to FIG. 2, showing how the FIG. 1 prior art cigarette paper (10, 10A) selectable environment might be augmented at 35 to provide a sub-generic first embodiment 30 of the "therapeutically enhanced saliva-activatable cellulosic product" of the present invention.
Figure 4:
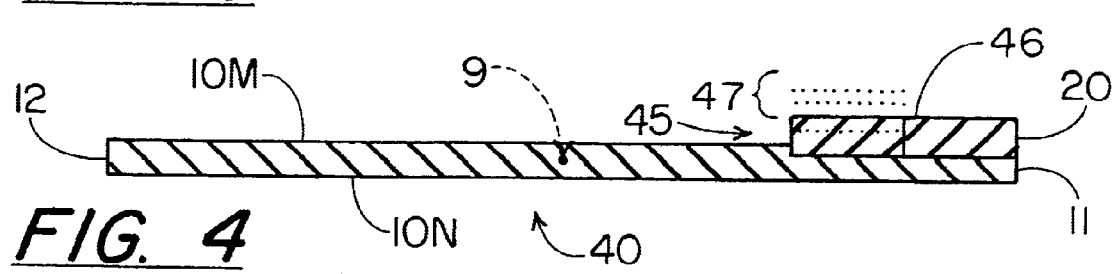
FIG. 4 is a sectional elevational view, similar to FIGS. 2 and 3, showing how the FIG. 1 prior art cigarette paper (10, 10A) selectable prior art environment might be augmented at 45 to provide a sub-generic second embodiment 40 of the "therapeutically enhanced saliva-activatable cellulosic product" of the present invention.

Turning serially next to: drawing FIG. 3 which alludes to a multi-species first embodiment (30) based upon the selectable cigarette paper prior art environment (10, 10A); and to drawing FIG. 4 which alludes to a multi-species second embodiment (40) similarly based upon the selectable cigarette paper prior art environment (10, 10A). Although in both said multi-species embodiments (30, 40) there is provided a second-strip (35, 45) of adhesive material located atop upper-surface 10M and located alongside adhesive first-strip 20 toward central-axis 9, the first embodiment's second-strip 35 is necessarily hydrophilic, but the second embodiment's second-strip 45 might be hydrophobic.

As suggested by the sectionally depicted multi-dots portion located at the upper portion of the hydrophilic adhesive second-strip (35) of the drawing FIG. 3 first embodiment (30), such multi-dots indicated therapeutic agent is topically miscible within the saliva-activatable hydrophilic second-strip 35 and without denigrating the original solid state thereof. Accordingly, whenever an encountered user saliva-wise actuates the second-strip (35) the topical therapeutic agent therat (37) will be concommitently ingested into the user. Numerous hydrophilic second-strip adhesives are adequate including, inter alia, polyvinyl alcohol, methyl cellulose, gelatines, musilage, gum arabic, etc. And for miscible therapeutic agents adequate are: aspirin, polyvinyl acetate phthalate, etc.

As suggested by the topical stratum 47 overlying the hydrophobic second-strip adhesive (45) of the drawing Figure second embodiment (40), the ingestible adhesive is loosely (though ingestibly) topically maintained. Such hydrophobia adhesives might be selected from: ethyl acetate, proteins, etc. And the topically applued therapeutic agents might be selected from aspirin, dicalcium phosphate, etc.

As a possible alternative to the generic cellulosic paper environment (e.g. cigarette paper 10, 10A, of drawing FIG. 1 ) and for the "therapeutically enhanced saliva-activatable cellulosic product" objective of the present invention, an alternative environment might be a conventional cellulosic mailing envelope as typically depicted (as 100) in prior art drawing FIGS. 5 and 6. A such typical mailing envelope (e.g.

100) is basically fabricated of a single laminar sheet of cellulosic paper that is directional longitudinally folded (PF) to thusly provide an upper-panel (101) overlying an outwardly directionally transversely wider lower-panel (102), the latter having a pair of broad parallel horizontal surfaces including an upper-surface 103M overlying a lower-surface 103N. The transversely outward extremity of lower-panel 102 takes the form of a more-or-less longitudinal—edge 104. Atop such upper-surface 103M and alongside upright longitudinal—edge 104 is a saliva-activatable normally-solid first-strip adhesive-layer 105 (having a topical-surface 106) conventionally provided of such normally-solid substances as gelatine, musilage, gum arabic, polyvinyly alcohol, or the like.

As suggested in drawing FIG. 7, a such drawing FIGS. 5 & 6 mailing envelope environment (e.g. 100) might be modified into a structure (130) meeting the objectives of the present invention by: miscibly providing the adhesive-layer at its topical-surface 106 with a saliva-activatable and injestible therapeutic-agent (107) that suitably non-interferes with the normally-solid integrity of the prior art adhesive-layer (105). Such phasewise non-interfering therapeutic-agents might include: for topically (106) swabbable liquids, liquid-aspirin, polyvinyl acetate phthaate, etc; and for comminutated soids topically (106) sprinkable at temporarily moistable states of the adhesive-layer (105) such as granular-aspirin, dicalcium phosphate, etc.

From the foregoing, the Therapeutically Enhanced Saliva-Activatable Cellulosic Products ideas of the present invention will be readily understood and further explanation is believed to be unnecessary. However, since numerous modifications and changes will be appreciated by those skileed in the art, it is not desired to limit the invention to the exact modes described hereabove, and accordingly, all modifications ions and equivalents might be resorted to, falling within the scope of the appended claims.

I claim:

1. Therapeutically Enhanced Saliva-Activatable Cellulosic Product comprising a flexibly rollable conventional cellulosic, cigarette paper item having parallel horizontal broad surfaces including an upper-surface and a lower-surface both extending directionally longitudinally along a central-axis that is flanked by two longitudinally extending upright lengthwise-edges, said conventional cellulosic cigarette paper item having along a first longitudinal-edge at said upper-surface a saliva-moistable first-strip adhesive-layer, a longitudinally extending second-strip adhesive-layer located at said upper-surface between said first-strip and said central-axis, said second-strip carrying at a directionally longitudinal topical-surface thereof, a saliva activaiable therapudic agent selected from a group consisting of aspirin and polyvinyl acetate phthalate.

2. The Therapeutically Enhanced Saliva-Activatable Cellulosic Product of claim 1 wherein the conventional flexibly rollable cellulosic cigarette paper dfinite longitudinal-length between a frontal-edge and a rearward-edge both transversely perpendiculary intersection said central-axis; and wherein each said first-strip and said second-strip respectively extend for major proportional longitudinal lengths between said forward-edge and rearward-edge.

3. The structure of claim 1 wherein the second-strip adhesive portion is hydrophilic.

4. The structure of claim 1 wherein the therapeutic agent is liquid and is uniphase miscible with said hydrophilic adhesive portion.

5. The structure of claim 2 wherein the second-strip adhesive portion is hydrophilic; and wherein the therapeutic agent is liquid and is in a solid plasticizing relationship with said hydrophilic adhesive portion.

6. The structure of claim 2 wherein the wherein the therapeutic agent, has the physical form of a comminutated solid in admixture within said hydrophilic second-strip adhesive portion.

7. The structure of claim 1 wherein the second-strip adhesive portion is hydrophilic; and wherein the therapeutic agent has the physical form of a comminutated solid that is yieldably secured at the adhesive portion topical area under the influence of orally deposited saliva.

8. Therapeutically Enhanced Saliva-Activatable Cellulosic Product environmentally comprising a conventional cellulosic mailing envelope having a foldable flap portion directionally longitudinally provided with a first-strip adhesive-layer and with a saliva-activatable therapeutic agent located at the topical surface of said first-strip adhesive-layer.

9. The structure of claim 8 wherein the therapeutic agent is normally liquid and has a solid plasticizing relationship with said hydrophilic first-strip adhesive-layer.

10. The structure of claim 1 wherein the therapeutic agent has the physical form of a comminutated solid in admixture with said hydrophilic second-strip adhesive portion.

* * * * *